United States Patent [19]
Suzuki et al.

[11] Patent Number: 5,869,744
[45] Date of Patent: Feb. 9, 1999

[54] OXYGEN CONCENTRATION-DETECTING DEVICE FOR INTERNAL COMBUSTION ENGINES

[75] Inventors: Norio Suzuki; Daisuke Shimizu; Koichi Saiki; Yukio Noda, all of Wako, Japan

[73] Assignee: Honda Giken Kogyo Kabushiki Kaisha, Tokyo, Japan

[21] Appl. No.: 953,726

[22] Filed: Oct. 17, 1997

[30] Foreign Application Priority Data

Oct. 18, 1996 [JP] Japan ................................ 8-297397
Oct. 18, 1996 [JP] Japan ................................ 8-297398

[51] Int. Cl.$^6$ ..................................................... G01N 27/41
[52] U.S. Cl. ........................................... 73/23.32; 73/118.1
[58] Field of Search .............................. 73/23.31, 23.32, 73/118.1; 60/276, 277; 123/688

[56] References Cited

U.S. PATENT DOCUMENTS

| | | | |
|---|---|---|---|
| 3,933,028 | 1/1976 | Laud et al. | 73/23.32 |
| 4,505,246 | 3/1985 | Nakajima et al. | 73/23.32 |
| 4,742,808 | 5/1988 | Blumel et al. | 73/23.32 |
| 4,938,194 | 7/1990 | Kato et al. | 123/479 |
| 5,179,929 | 1/1993 | Miyashita et al. | 123/688 |
| 5,279,145 | 1/1994 | Suzuki | 73/23.32 |
| 5,507,174 | 4/1996 | Friese et al. | 73/23.32 |
| 5,524,472 | 6/1996 | Hotzel | 73/23.32 |
| 5,686,654 | 11/1997 | Friese et al. | 73/23.32 |
| 5,724,952 | 3/1998 | Miyashita et al. | 60/277 |

FOREIGN PATENT DOCUMENTS 59-163556  9/1984  Japan .

*Primary Examiner*—George M. Dombroske
*Attorney, Agent, or Firm*—Nikaido, Marmelstein, Murray & Oram LLP

[57] ABSTRACT

An oxygen concentration-detecting device detects the concentration of oxygen present in exhaust gases emitted from an internal combustion engine. The device includes an oxygen sensor of a limit current type. A heater heats the oxygen sensor. A first voltage is applied to the oxygen sensor and the concentration of oxygen is detected based on a first output current from the oxygen sensor obtained when the first voltage is applied to the oxygen sensor. A second voltage is applied to the oxygen sensor at a first repetition period and the internal resistance of the oxygen sensor is detected based on a second output current from the oxygen sensor obtained when the second voltage is applied to the oxygen sensor. The oxygen sensor is heated by the heater based on the internal resistance of the oxygen sensor detected. Values of the concentration of oxygen are sampled based on the first output current from the oxygen sensor at a second repetition period shorter than the first repetition period and the sampled values of the concentration of oxygen are stored. The concentration of oxygen is estimated based on the sampled values of the concentration of oxygen stored. In another form of the invention, a predetermined repetition period (first repetition period) at which the second voltage is applied is set in dependence on operating conditions of the engine.

9 Claims, 10 Drawing Sheets

OXYGEN CONCENTRATION-DETECTING DEVICE FOR INTERNAL COMBUSTION ENGINES

BACKGROUND OF THE INVENTION

1. Field of the Invention

This invention relates to an oxygen concentration-detecting device for internal combustion engines, which detects the concentration of oxygen present in exhaust gases emitted from an internal combustion engine, and more particularly to an oxygen concentration-detecting device of this kind which employs an oxygen sensor of a limit current type (hereinafter referred to as "the LAF sensor").

2. Prior Art

Conventionally, an oxygen concentration-detecting device of this kind has been proposed, e.g. by Japanese Laid-Open Patent Publication (Kokai) No. 59-163556, which utilizes an output from the LAF sensor having a characteristic that when the temperature of the LAF sensor is within an activation temperature range, the sensor output current exhibits a value proportional to partial pressure of oxygen in exhaust gases if a certain positive voltage is applied to the sensor, to thereby linearly detect the concentration of oxygen present in the exhaust gases. The LAF sensor has a limit current characteristic which varies with the temperature thereof. Therefore, to maintain the accuracy of detection of the oxygen concentration, it is required to constantly control the temperature of the LAF sensor such that it is within the activation temperature range. To meet this requirement, the proposed oxygen concentration-detecting device utilizes a characteristic of the LAF sensor that when a negative voltage is applied to the sensor, the value of the sensor output current is not dependent on the partial pressure of oxygen but proportional to the temperature of the LAF sensor. More specifically, the proposed device detects the internal resistance of the LAF sensor by applying a predetermined negative voltage to the sensor, and heats the LAF sensor with a heater such that the detected internal resistance of the LAF sensor is held constant, to thereby maintain the LAF sensor in the active state.

However, since the oxygen concentration in exhaust gases and the internal resistance of the LAF sensor are detected by applying respective different values of voltage (the predetermined positive voltage and the predetermined negative voltage) to the LAF sensor, they cannot be detected concurrently. Therefore, the applied voltage is changed over between the predetermined positive voltage and the predetermined negative voltage at predetermined time intervals (in a time-sharing manner) to thereby alternately detect them.

Generally, the output from the LAF sensor is utilized for various kinds of control. For example, the output from the LAF sensor is used in air-fuel ratio feedback control of an internal combustion engine based on a modern control theory, in which fine control is carried out based on the output from the LAF sensor by using a controller of a recurrence formula type, such as an observer and an optimal regulator. In this control, the optimal value has to be selected from a group of samples of the LAF sensor output. This requires the sensor output to be sampled at a very short sampling period.

In the oxygen concentration-detecting device proposed by Japanese Laid-Open Patent Publication (Kokai) No. 59-163556, however, the detection of the oxygen concentration is suspended at least during a time period over which the internal resistance of the LAF sensor is detected, and therefore actual or true detected values of the oxygen concentration are not obtained during the time period. Moreover, the time period of detection of the internal resistance of the LAF sensor comes round at the predetermined time intervals irrespective of operating conditions of the engine (hereinafter, the period at which comes round the time of detection of the internal resistance will be referred to as "the internal resistance detection repetition period"). Therefore, if the internal resistance detection repetition period is set to a very short period, the detection of the oxygen concentration is suspended more frequently, which causes the observer, for example, to make inaccurate estimation of air-fuel ratios of exhaust gases from the cylinders of the engine (cylinder-by-cylinder air-fuel ratio), resulting in inability to properly achieve fine control as intended.

More specifically, in the observer, a value of the oxygen concentration detected immediately before the start of detection of the internal resistance of the LAF sensor is held until the start of the next detection of the oxygen concentration, and the held value of the oxygen concentration is regarded as values of the same detected over the time period during which the detection of the oxygen concentration is suspended (suspension period). If the held value is selected as samples of the LAF sensor output to be obtained during the suspension period, the value of the oxygen concentration thus selected as a value for the desired cylinder (e.g. #2) can be closer to the actual value of the oxygen concentration of exhaust gases from the immediately preceding cylinder (e.g. #4) than a value which should be actually detected from exhaust gases from the desired cylinder (#2). In such a case, the difference between the air-fuel ratio value estimated based on the above held value and the actual or true air-fuel ratio value becomes large, leading to inaccurate estimation of the cylinder-by-cylinder air-fuel ratio. As a result, the air-fuel ratio feedback control cannot converge the air-fuel ratio of a mixture supplied to the engine to a desired air-fuel ratio or the air-fuel ratio of the mixture diverges. Especially, when the operating cycle of the engine and the internal resistance detection repetition period are almost synchronous with each other, it can occur that the air-fuel ratio of exhaust gases from a particular cylinder cannot be accurately detected at all, exerting a large adverse effect on the estimation of the cylinder-by-cylinder fuel-air ratio.

Thus, the proposed oxygen concentration-detecting device still remains to be improved in reaching the full potentials of various kinds of fine control which use values of the oxygen concentration detected by the LAF sensor, such as control based on the modern control theory.

Further, even in a type of control which does not require values of the LAF sensor output sampled at a short sampling period, if the frequency of coincidence of timing requiring a detected value of the oxygen concentration with the internal resistance-detecting period is high, this can degrade the air-fuel ratio controllability. Therefore, to decrease the frequency of coincidence, it is desirable to set the internal resistance detection repetition period as long as possible.

However, if the internal resistance detection repetition period is set too long, it is difficult to constantly maintain the temperature of the LAF sensor within the activation temperature range. For example, a delay of control of the temperature of the sensor element of the LAF sensor occurs due to the excessively long internal resistance detection repetition period when the temperature of exhaust gases suddenly changes, e.g. upper fuel cut of the engine. As a result, the accuracy of detection of the oxygen concentration by the LAF sensor is degraded.

Thus, if the internal resistance detection repetition period is uniformly set to a fixed value, there can arise inconveniences depending on operating conditions of engine.

SUMMARY OF THE INVENTION

It is a first object of the invention to provide an oxygen concentration-detecting device for an internal combustion engine, which is capable of improving the accuracy of various types of control using an output from an oxygen sensor of a limit current type.

It is a second object of the invention to provide an oxygen concentration-detecting device for an internal combustion engine, which is capable of minimizing adverse effects of provision of the oxygen concentration detection suspension period, while maintaining the accuracy of detection of the oxygen concentration.

To attain the first object, according to a first aspect of the invention, there is provided an oxygen concentration-detecting device for detecting concentration of oxygen present in exhaust gases emitted from an internal combustion engine, including an oxygen sensor of a limit current type, heating means for heating the oxygen sensor, oxygen concentration-detecting means for applying a first voltage to the oxygen sensor and detecting the concentration of oxygen based on a first output current from the oxygen sensor obtained when the first voltage is applied to the oxygen sensor, internal resistance-detecting means for applying a second voltage to the oxygen sensor for a predetermined period at a first repetition period and detecting internal resistance of the oxygen sensor based on a second output current from the oxygen sensor obtained when the second voltage is applied to the oxygen sensor, and heating control means for controlling heating of the oxygen sensor by the heating means based on the internal resistance of the oxygen sensor detected by the internal resistance-detecting means.

The oxygen concentration-detecting device according to the first aspect of the invention is characterized by comprising:

memory means for sampling values of the concentration of oxygen based on the first output current from the oxygen sensor at a second repetition period shorter than the first repetition period and storing sampled values of the concentration of oxygen; and oxygen concentration-estimating means for estimating the concentration of oxygen based on the sampled values of the concentration of oxygen stored in the memory means when said second voltage is applied to said oxygen sensor.

Preferably, the oxygen concentration-estimating means estimates the concentration of oxygen by an interpolation based on one of the sampled values of the concentration of oxygen sampled immediately before the second voltage was applied to the oxygen sensor by the internal resistance-detecting means and stored in the memory means, and another one of the sampled values of the concentration of oxygen sampled immediately after the second voltage ceased to be applied to the oxygen sensor by the internal resistance-detecting means and stored in the memory means.

More preferably, the memory means has a predetermined number of storage areas, and stores the one of the sampled values of the concentration of oxygen sampled immediately before the second voltage was applied to the oxygen sensor by the internal resistance-detecting means sequentially into corresponding ones of the storage areas over a time period during which the internal resistance-detecting means detects the internal resistance of the oxygen sensor.

Further preferably, the oxygen concentration-detecting device includes selecting means for selecting one of the storage areas from which one of the sampled values of the concentration of oxygen is to be read out, in dependence on operating conditions of the engine.

Further preferably, the interpolation is carried out by using a number assigned to one of the storage areas which stores the one of the sampled values of the concentration of oxygen sampled immediately before the second voltage was applied to the oxygen sensor by the internal resistance-detecting means, the one of the sampled values of the oxygen concentration stored in the one of the storage areas, a number assigned to another one of the storage areas which stores the another one of the sampled values of the concentration of oxygen sampled immediately after the second voltage ceased to be applied to the oxygen sensor by the internal resistance-detecting means, and the another one of the sampled values of the oxygen concentration stored in the another of the storage areas.

To attain the second object, according to a second aspect of the invention, there is provided an oxygen concentration-detecting device for detecting concentration of oxygen present in exhaust gases emitted from an internal combustion engine, including an oxygen sensor of a limit current type, heating means for heating the oxygen sensor, detecting means for applying a first voltage to the oxygen sensor, detecting the concentration of oxygen present in exhaust gases emitted from the engine based on a first output current from the oxygen sensor obtained when the first voltage is applied to the oxygen sensor, applying a second voltage to the oxygen sensor for a predetermined period at a predetermined repetition period, and detecting internal resistance of the oxygen sensor based on a second output current from the oxygen sensor obtained when the second voltage is applied thereto, and heating control means for controlling heating of the oxygen sensor by the heating means based on the internal resistance of the oxygen sensor detected by the detecting means.

The oxygen concentration-detecting device according to the second aspect of the invention is characterized by comprising repetition period-setting means for setting the predetermined repetition period in dependence on operating conditions of the engine.

Preferably, when an air-fuel ratio of a mixture supplied to the engine assumes a lean value, the repetition period-setting means sets the predetermined repetition period to a shorter period than when the air-fuel ratio is richer than the lean value.

Further preferably, the repetition period-setting means determines that the air-fuel ratio of the mixture assumes the lean value when the first output current from the oxygen sensor obtained when the first voltage is applied to the oxygen sensor is larger than a predetermined value.

Preferably, the repetition period-setting means sets the predetermined repetition period to a shorter period when air-fuel ratio feedback control responsive to the first output current from the oxygen sensor is not carried out than when the air-fuel ratio feedback control is carried out.

The above and other objects, features, and advantages of the invention will be become more apparent from the following detailed description taken in conjunction with the accompanying drawings.

DETAILED DESCRIPTION

The invention will now be described in detail with reference to the drawings showing embodiments thereof.

Figure 1:
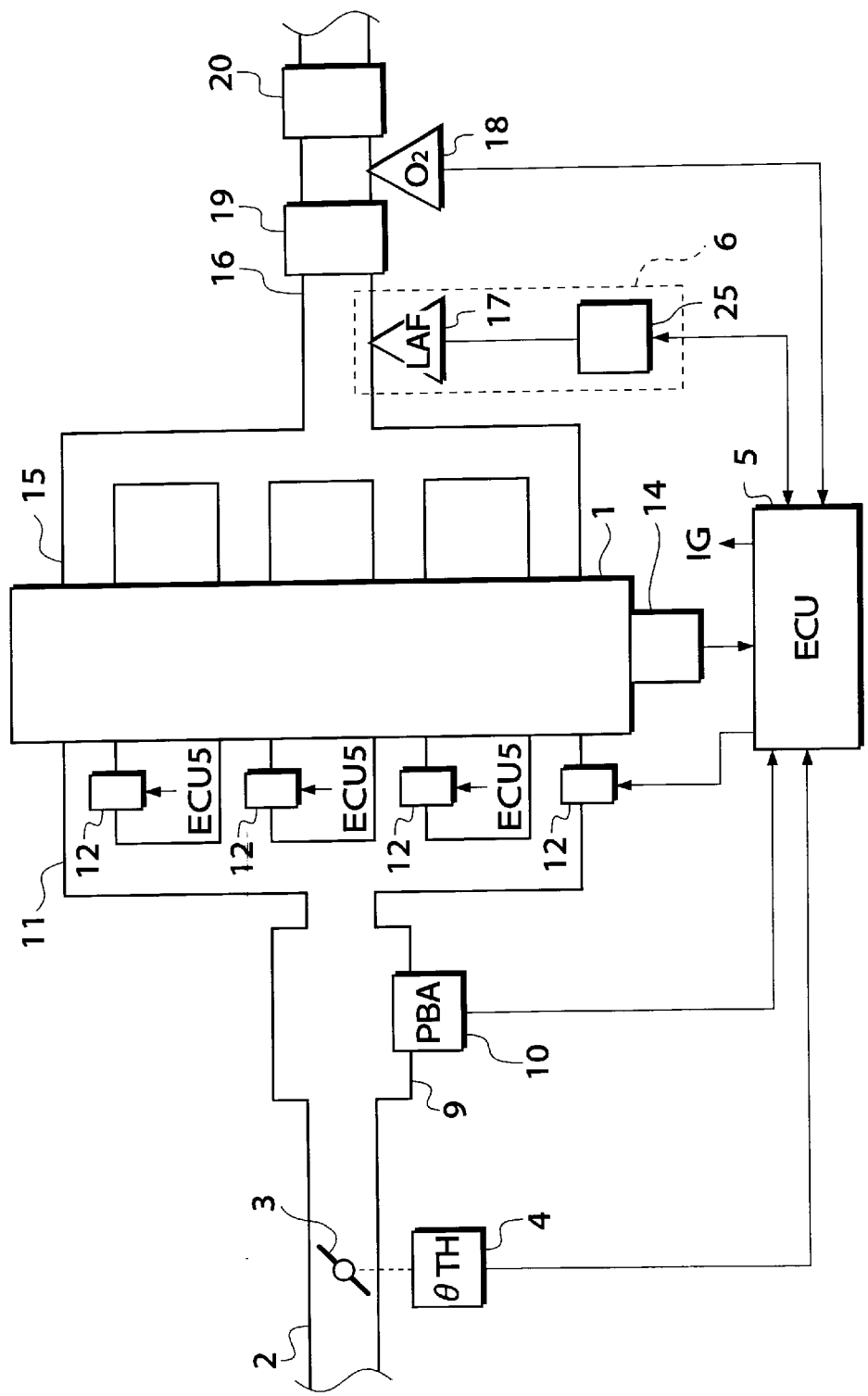
FIG. 1 is a block diagram showing the whole arrangement of a control system for an internal combustion engine incorporating an oxygen concentration-detecting device according to a first embodiment of the invention.

Referring first to FIG. 1, there is shown the whole arrangement of a control system for an internal combustion engine (hereinafter referred to as "the engine") incorporating an oxygen concentration-detecting device according to a first embodiment of the invention. In the figure, reference numeral 1 designates the engine.

The engine 1 has an intake pipe 2 having a manifold part (intake manifold) 11 connected to the combustion chamber of each cylinder of the engine 1. A throttle valve 3 is arranged in the intake pipe 2 at a location upstream of the manifold part 11. A throttle valve opening ($\theta$ TH) sensor 4 is electrically connected to the throttle valve 3 for generating an electric signal indicative of the sensed throttle valve opening $\theta$ TH and supplying the same to an electronic control unit (hereinafter referred to as "the ECU") 5.

A crank angle position sensor 14 for detecting the rotational angle of a crankshaft, not shown, of the engine 1 is connected to the cylinder block of the engine 1, and supplies signals corresponding to the rotational angle of the crankshaft to the ECU 5. The crank angle position sensor 14 is comprised of a cylinder-discriminating sensor which generates a pulse (hereinafter referred to as "the CYL signal pulse") at a predetermined crank angle position of a particular cylinder of the engine 1, a TDC sensor which generates a pulse (hereinafter referred to as "the TDC signal pulse") at a predetermined crank angle position of each cylinder a predetermined angle before a TDC position of the cylinder (whenever the crankshaft rotates through 180 degrees in the case of a four-cylinder engine), and a CRK sensor which generates a pulse (hereinafter referred to as "the CRK signal pulse") at each of predetermined crank angle positions whenever the crankshaft rotates through a predetermined angle (e.g. 30 degrees) smaller than the rotational angle interval of generation of the TDC signal pulse. The CYL signal pulse, the TDC signal pulse and the CRK signal pulse are supplied to the ECU 5. These signal pulses are used for timing control in carrying out operations of the control system for determining the fuel injection amount (fuel injection period), fuel injection timing, ignition timing, etc., as well as for detecting the engine rotational speed NE.

Fuel injection valves 12 for respective cylinders are inserted into the intake manifold 11 at locations slightly upstream of intake valves, not shown, of the respective cylinders. The fuel injection valves 12 are connected to a fuel pump, not shown, and electrically connected to the ECU 5 to have their valve opening periods (fuel injection periods) and fuel injection timing controlled by signals therefrom. The engine 1 has spark plugs, not shown, provided for respective cylinders and electrically connected to the ECU 5 to have ignition timing $\theta$ IG thereof controlled by signals therefrom.

An exhaust pipe 16 of the engine has a manifold part (exhaust manifold) 15 directly connected to the combustion chambers of the cylinders of the engine 1. A LAF sensor 17, which is of a limit current type, is inserted into a confluent portion of the exhaust pipe 16 at a location immediately downstream of the exhaust manifold 15. Further, an immediate downstream three-way catalyst 19 and a bed-downstream three-way catalyst 20 are arranged in the confluent portion of the exhaust pipe 16 at locations downstream of the LAF sensor 17 for purifying noxious components such as HC, CO, and NOx. An oxygen concentration sensor (hereinafter referred to as "the O2 sensor") 18 is arranged between the three-way catalysts 19 and 20.

As described hereinafter, the LAF sensor 17 forms the oxygen concentration-detecting device 6 together with an oxygen concentration detection and activation control device (hereinafter referred to as "the control device") 25. The LAF sensor 17 is electrically connected via the control device 25 to the ECU 5 for supplying the control device 25 with an electric signal substantially proportional in value to the concentration of oxygen present in exhaust gases emitted from the engine (i.e. the air-fuel ratio of a mixture supplied to the engine). A detected value of the oxygen concentration is stored in the control device 25 and read out by the ECU 5. The processing of detected values of the oxygen concentration will be described hereinafter. The O2 sensor 18 has an output characteristic that output voltage thereof drastically changes when the air-fuel ratio of the mixture supplied to the engine changes across a stoichiometric air-fuel ratio, and generates a high level signal when the mixture is richer than the stoichiometric air-fuel ratio, and a low level signal when the mixture is leaner than the same. The O2 sensor 18 supplies the ECU 5 with the high or low level signal.

The ECU 5 is comprised of an input circuit having the functions of shaping the waveforms of input signals from various sensors including the above-mentioned ones, shifting the voltage levels of sensor output signals to a predetermined level, converting analog signals from analog-output sensors to digital signals, and so forth, a central processing unit (hereinafter referred to as "the CPU"), a memory device comprised of a ROM storing various operational programs which are executed by the CPU and various maps, described hereinafter, and a RAM for storing results of calculations from the CPU, etc., and an output circuit which outputs driving signals to the fuel injection valves 12 and other electromagnetic valves, the spark plugs, etc.

The ECU 5 operates in response to the above-mentioned signals from the sensors to determine various operating conditions in which the engine 1 is operating, such as an air-fuel ratio feedback control region in which the air-fuel ratio is controlled in response to outputs from the LAF sensor 17 and the O2 sensor 18, and air-fuel ratio open-loop control regions other than the air-fuel ratio feedback control region, and calculates, based upon the determined operating conditions, the valve opening period or fuel injection period TOUT over which the fuel injection valves 12 are to be opened, by the use of the following equation (1) in synchronism with inputting of. TDC signal pulses to the ECU 5, to deliver driving signals to the fuel injection valves 12, which are based on results of the calculation:

$$TOUT = TIMF \times K1 + K2 \qquad (1)$$

where TIMF represents a basic fuel amount, or more specifically, a basic fuel injection period, which is determined in accordance with the engine rotational speed NE and the intake pipe absolute pressure PBA. K1 and K2 represent correction coefficients and correction variables, respectively, which are-set according to engine operating parameters to such values as optimize operating characteristics of the engine, such as fuel consumption and engine accelerability.

The ECU 5 further supplies signals indicative of air-fuel ratio control conditions and the like to the control device 25.

Figure 2:
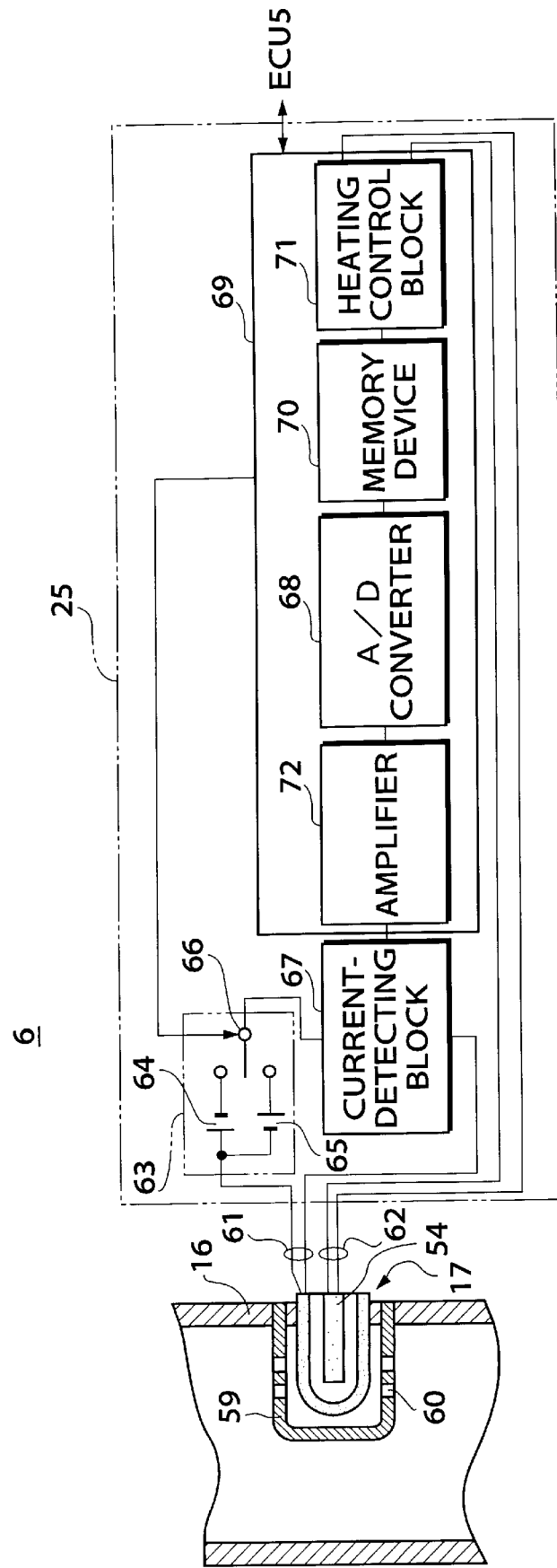
FIG. 2 is a block diagram showing details of the construction of the oxygen concentration-detecting device according to the first embodiment.

FIG. 2 shows details of the construction of the oxygen concentration-detecting device 6 according to the first embodiment.

The oxygen concentration-detecting device 6 is comprised of the LAF sensor 17 and the control device 25. The LAF sensor 17 is inserted into the exhaust pipe 16 of the engine 1, as mentioned above, and has an output signal line thereof detachably connected to the control device 25 by a connector, not shown. The LAF sensor 17 is comprised of a solid electrolyte element, and so forth, with a heater 54 mounted therein. The heater 54 has a sufficient heating capacity for activating the LAF sensor 17. Further, the LAF sensor 17 is enclosed within a cover 59 formed with small through holes 60 for permitting exhaust gases to flow into the cover 59, whereby the LAF sensor 17 is prevented from being directly exposed to exhaust gases flowing in the exhaust pipe 16 for the purpose of protection and heat insulation thereof.

The control device 25 is provided with a bias control block 63, a current-detecting block 67, and a control block 69. One of two lead wires 61 connected to the LAF sensor 17 is connected to the bias control block 63, whereas the other of the lead wires 61 is connected to the current-detecting block 67. Two lead wires 62 connected to the heater 54 are connected to a heating control block 71 of the control block 69.

The bias control block 63 has a positive bias source 64, a negative bias source 65, and a-selector switch 66. The current-detecting block 67 is connected to the selector switch 66 and the control block 69. The selector switch 66 is connected to the control block 69, as well. The selector switch 66 changes over the polarity of the voltage to be applied to the LAF sensor 17, in response to a signal from the control block 69, whereas the current-detecting block 67 detects output current from the LAF sensor 17 and delivers a signal indicative of the detected current to the control block 69.

The control block 69 is comprised of an amplifier 72 for amplifying the signal input from the current-detecting block 67 and shaping the waveform thereof, an A/D converter 68 for converting the amplified signal in analog form to a signal in digital form, a memory device 70, and the heating control block 71 for controlling heating conditions of the heater 54. The memory device 70 is comprised of a ROM storing various operational programs which are executed by the control block 69 and various maps, described hereinafter, and a RAM for storing results of calculations from the control block 69, etc., a ring buffer memory for storing values of the oxygen concentration (air-fuel ratio A/F) detected by the LAF sensor 17, and so forth. This ring buffer memory is divided into e.g. twelve storage areas (buffers) in the present embodiment.

The control block 69 receives the CYL signal pulse, the TDC signal pulse, and the CRK signal pulse from the ECU 5. Further, the control block 69 receives the above-mentioned signals indicative of the air-fuel ratio control conditions, as well as other signals indicative of operating conditions of the engine, such as a signal indicative of the engine rotational speed NE and a signal indicative of the intake pipe absolute pressure PBA. On the other hand, the control block 69 supplies the ECU 5 with a signal indicative of a detected value of the oxygen concentration selected by a process described hereinafter.

The LAF sensor 17 has an operating characteristic that the limit current is proportional to partial pressure of oxygen in exhaust gases when a predetermined positive voltage V1 is applied to the LAF sensor 17, whereby the concentration of oxygen in exhaust gases can be linearly detected. However, to activate the LAF sensor 17, it is required to heat the same to a high temperature (approximately 650° C.), and moreover the temperature range within which the LAF sensor 17 can be active (activation temperature range) is narrow. Therefore, the temperature of the LAF sensor 17 cannot be held within the activation temperature range only by the heat of exhaust gases from the engine 1. Therefore, it is required to maintain the LAF sensor 17 active by detecting the internal resistance of the LAF sensor 17 (hereinafter referred to as "the LAF sensor-activating process"). The oxygen concentration-detecting device 6 alternately carries out the LAF sensor-activating process and a process for detecting the oxygen concentration (hereafter, referred to as "the oxygen concentration-detecting process") at a predetermined switching period T. The switching period T for switching between the LAF sensor-activating process and the oxygen concentration-detecting process is set based on the heat capacities of the sensor element of the LAF sensor 17 and the heater 54, the cooling characteristic of the LAF sensor 17, the activation temperature range of the LAF sensor 17, and so forth.

Figure 3:
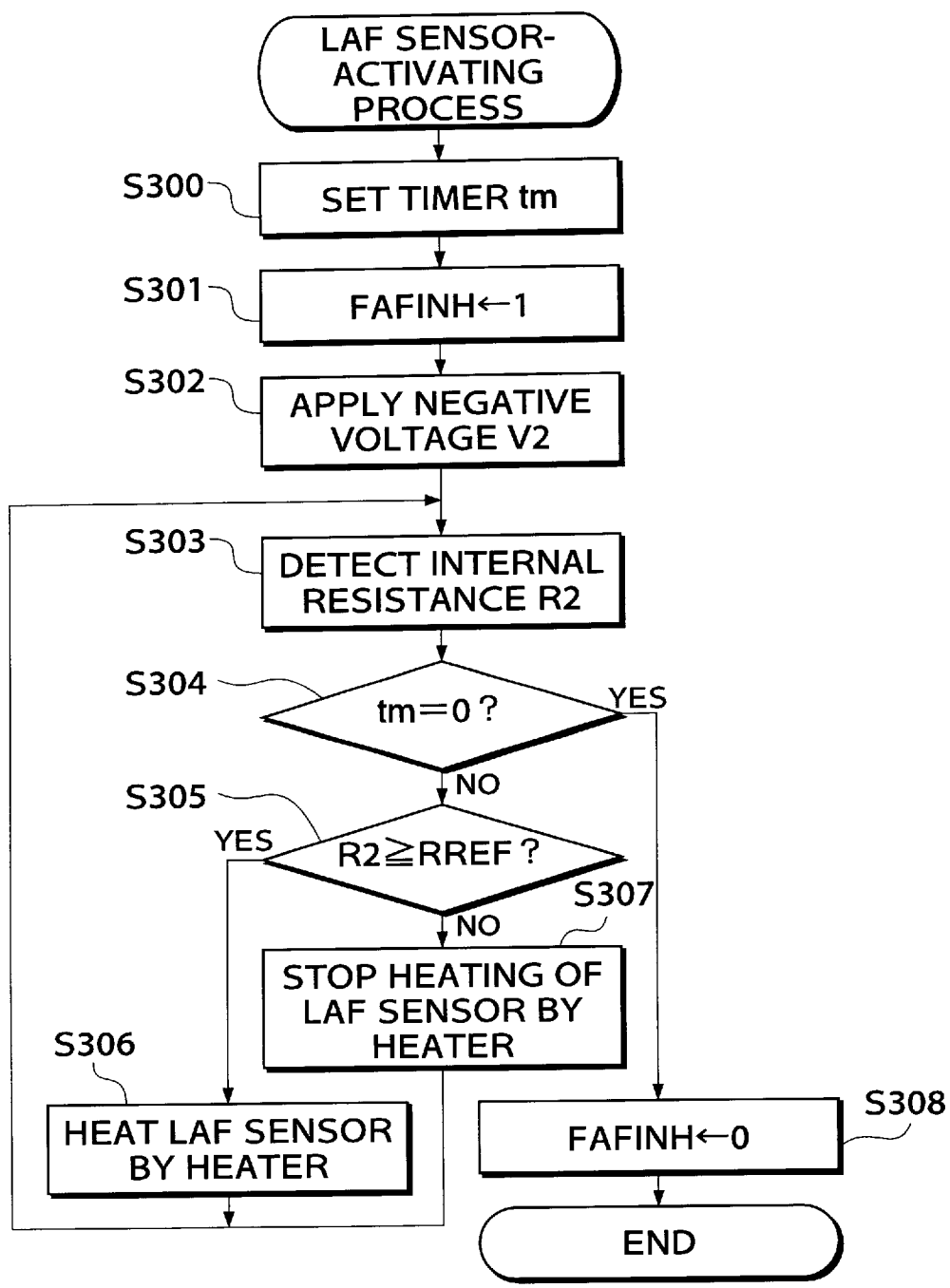
FIG. 3 is a flowchart showing a routine for carrying out a LAF sensor-activating process, according to the first embodiment.

FIG. 3 shows a routine for carrying out the LAF sensor-activating process, which is executed by the control block 69 at time intervals of the switching period T (e.g. 128 ms) set by a timer.

First, a resistance-detecting timer tm is set to a predetermined value (e.g. 4.5 ms) and started at a step S300, and then a flag FAFINH which, when set to 1, indicates that the internal resistance R2 of the LAF sensor is being detected, that is, the LAF sensor-activating process is being carried out, is set to 1 at a step S301. Then, the selector switch 66 is connected to the negative bias source 65 at a step S302, whereby a predetermined negative voltage V2 is applied to the LAF sensor 17, and then the internal resistance R2 of the LAF sensor 17 is detected in the following manner at a step S303:

A value I2 of output current from the LAF sensor 17 obtained when the predetermined negative voltage V2 is applied thereto is detected by the current-detecting block 67. The signal indicative of the detected current value I2 is amplified and shaped by the amplifier 72, and converted into a digital signal by the A/D converter 68. The internal resistance R2 of the LAF sensor 17 is detected based on this digital signal.

Then, it is determined at a step S304 whether or not the resistance-detecting timer tm has counted down to 0. If the count of the resistance-detecting timer tm is not equal to 0, it is determined at a step S305 whether or not the internal resistance R2 detected at the step S303 is equal to or higher than a predetermined reference value RREF. If R2≧RREF holds, the heating control block 71 is instructed to cause the heater 54 to heat the LAF sensor 17 at a step S306, and then the program returns to the step S303. On the other hand, if R2<RREF holds, the heating control block 71 is instructed to cause the heater 54 to stop heating the LAF sensor 17 at a step S307, and then the program returns to the step S303. This controls the heating of the heater 54 such that the detected value of the internal resistance of the LAF sensor 17 is always constant, thereby constantly maintaining the temperature of the LAF sensor 17 within the activation temperature range.

On the other hand, if the count of the resistance-detecting timer tm has become equal to 0 at the step S304, the flag FAFINH is set to 0 at a step S308, followed by terminating the program.

Figure 4:
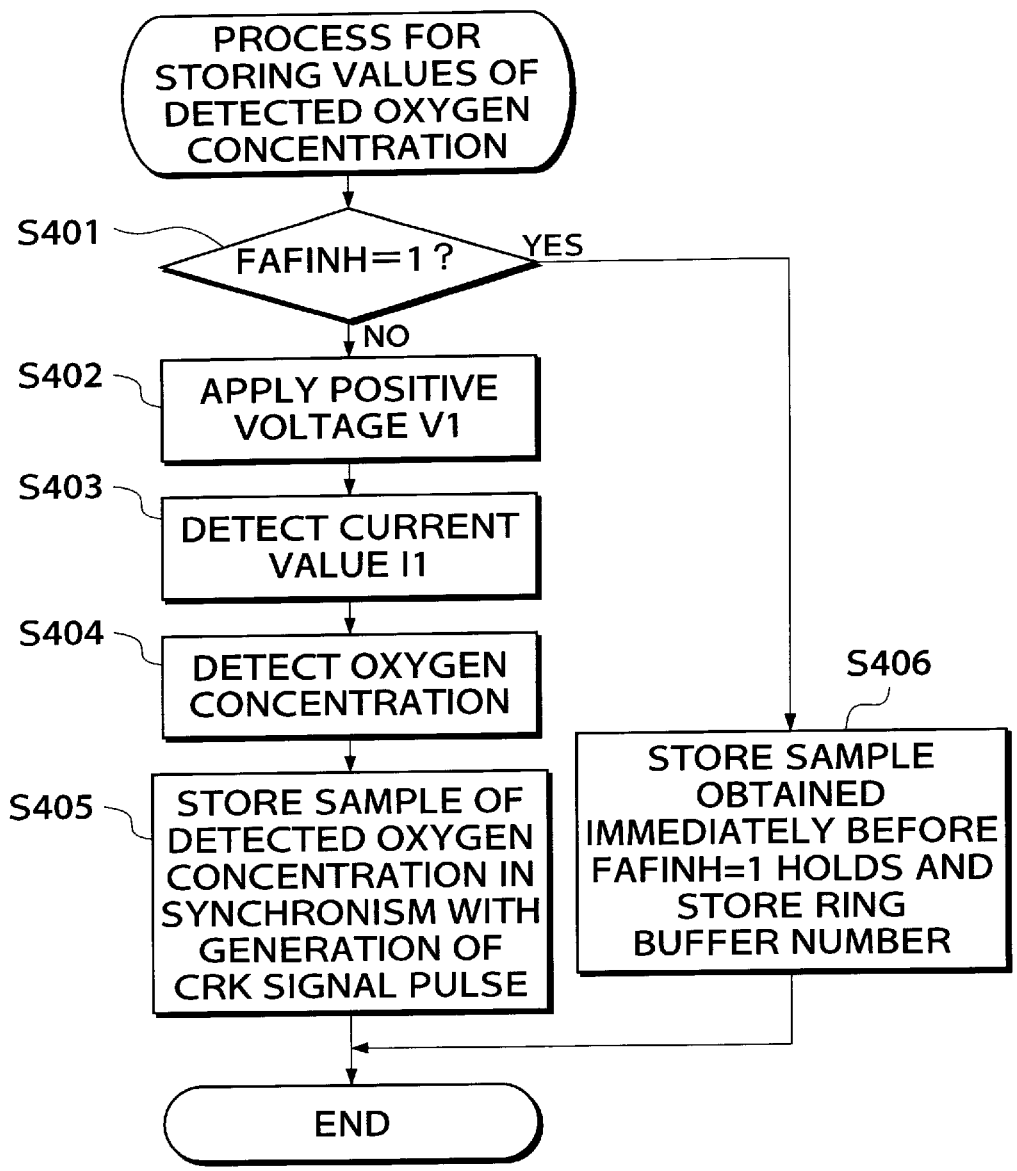
FIG. 4 is a flowchart showing a routine for carrying out a process for detecting the oxygen concentration in exhaust gases and storing detected values of the oxygen concentration, according to the first embodiment.

FIG. 4 shows a routine for carrying a process for detecting the oxygen concentration and storing detected values of the oxygen concentration. This routine is executed in synchronism with generation of each CRK signal pulse by the control block 69.

First, it is determined at a step S401 whether or not the flag FAFINH assumes 1. If the flag FAFINH does not assume 1, it means that it is within the time period for execution of the oxygen concentration-detecting process. Then, the selector switch 66 is connected to the positive bias resource 64, whereby the predetermined positive voltage V1 is applied to the LAF sensor 17 at a step S402. Then, a value I1 of the output current from the LAF sensor 17 is detected by the current-detecting block 67 at a step S403, and the signal indicative of the detected current value I1 is amplified and shaped by the amplifier 72, and then converted into a digital signal by the A/D converter 68. The concentration of oxygen in exhaust gases (air-fuel ratio) is detected based on the digital signal by retrieving a map, not shown, at a step S404. Then, the thus detected value (sample) of the oxygen concentration, which is sampled from the output from the LAF sensor 17 in synchronism with generation of each CRK signal pulse, is stored in the ring buffer memory of the memory device 70 at a step S405, followed by terminating the program.

On the other hand, if it is determined at the above step S401 that the flag FAFINH assumes 1, the program proceeds to a step S406, wherein the detected value of the oxygen concentration sampled immediately before the flag FAFINH was set to 1 is stored in the ring buffer memory of the memory device 70, and at the same time the number of a storage area in the ring buffer memory in which the detected value of the oxygen concentration is stored, followed by terminating the program.

Figure 5:
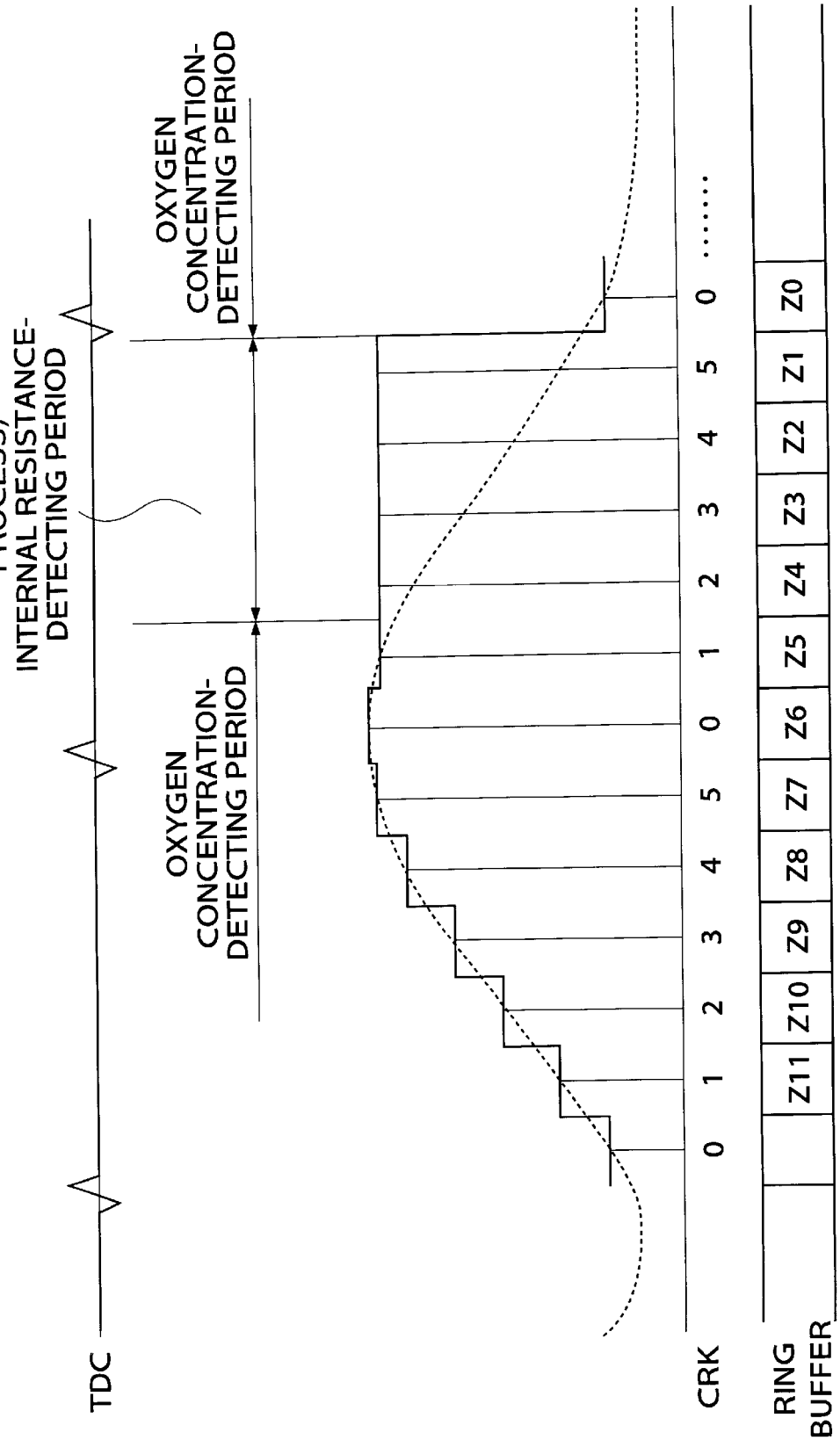
FIG. 5 is a diagram which is useful in explaining a manner of storing the detected values of the oxygen concentration by the FIG. 4 routine.

FIG. 5 shows an example of a manner of storing the detected values of the oxygen concentration by the FIG. 4 process. As shown in the figure, the curve (broken line) indicates changes in the analog value of the output from the LAF sensor 17, whereas the stepped solid line represents sampled values (digital values) of the detected value of the oxygen concentration obtained by sampling.

The present embodiment is applied to engine control, and hence the sampling period of the oxygen concentration is synchronized with the repetition period of generation of CRK signal pulses (crank angle intervals of 30 degrees) shorter than the switching period T. Six CRK signal pulses (No.0 to No.5) are generated during the repetition period of generation of each TDC signal pulse.

In the figure, the numbers with a prefix Z each designate a number assigned to one of the storage areas (twelve storage areas) of the ring buffer memory of the memory device 70 to indicate that the sampled value was obtained sampling times corresponding to the number with the prefix Z earlier than the present time.

As shown in the figure, during a time period over which the oxygen concentration-detecting process is carried out (oxygen concentration-detecting period), digital values of the detected oxygen concentration each obtained by sampling in synchronism with generation of each CRK signal pulse (at crank angle intervals of 30 degrees) are sequentially stored in the storage areas of the ring buffer memory (Z11 to Z5 in the illustrated example), whereas, during a time period over which the internal resistance-detecting process is carried out (internal resistance-detecting period), the output from the LAF sensor 17 as a signal indicative of the detected oxygen concentration value is not obtained, as described above, but a detected value of the oxygen concentration (value stored at a a storage area Z5) which was sampled immediately before the internal resistance-detecting process was started is successively stored in storage areas of the ring buffer memory (storage areas Z4 to Z1). That is, in the illustrated example, during the internal resistance-detecting period, the value stored in the storage area Z5 is held as the detected value of the oxygen concentration. Immediately after the oxygen concentration-detecting process is resumed, a new sample or digital value of the detected oxygen concentration is stored in the ring buffer memory (at a storage area Z0).

Figure 6:
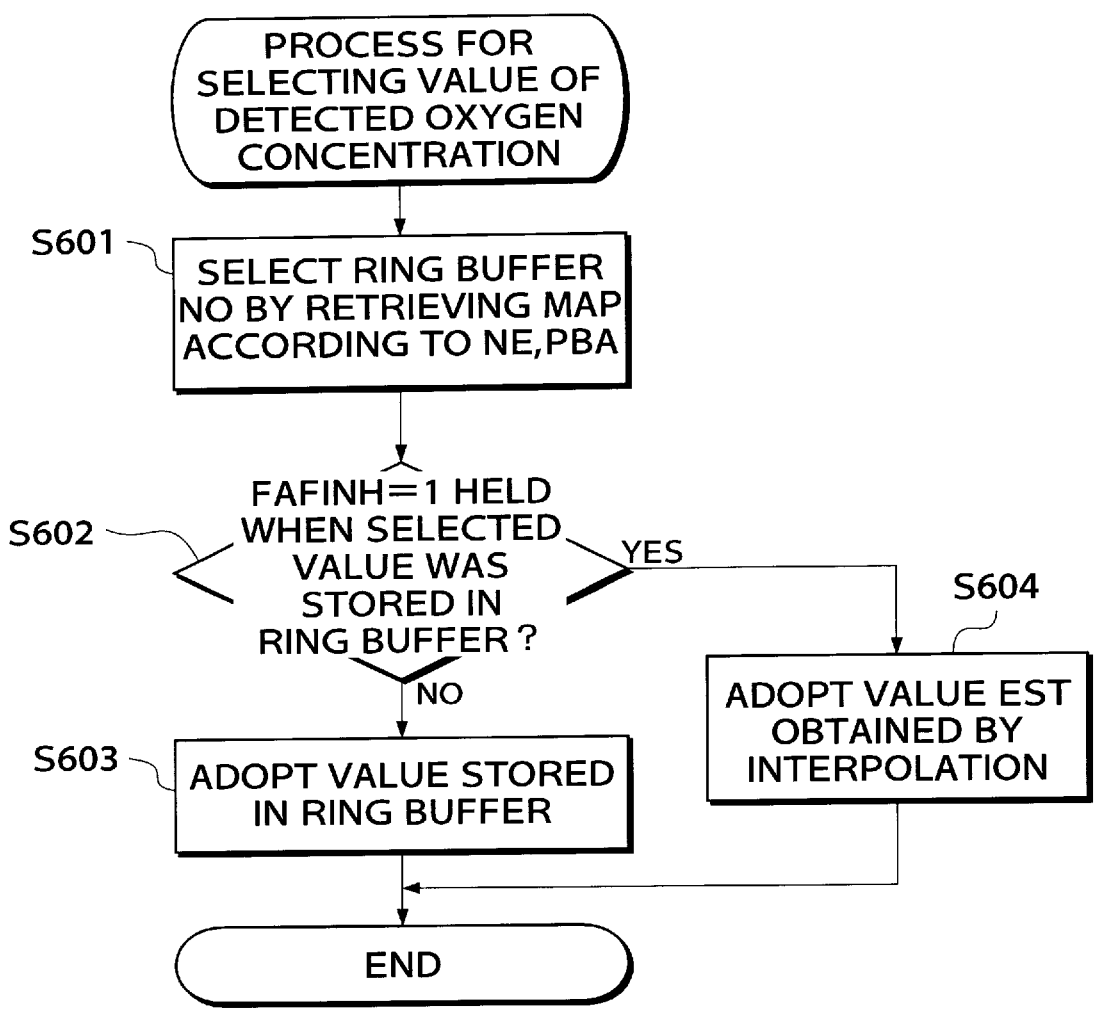
FIG. 6 is a flowchart showing a routine for carrying out a process for selecting a value of the detected oxygen concentration, according to the first embodiment.

FIG. 6 shows a routine for carrying out a process for selecting a detected value of the oxygen concentration, which is executed in synchronism with generation of each TDC signal pulse by the control block 69.

First, from the storage areas in the ring buffer memory which store detected values of the oxygen concentration, i.e. a value sampled eleven sampling times earlier to the present value, a storage area in the ring buffer memory, that is assigned with a number "ZN" indicative of a storage area which stores the optimum oxygen concentration value sampled at the optimum timing, is selected by retrieving a timing map according to the engine rotational speed NE and the intake pipe absolute pressure PBA, at a step S601.

Generally, when the detected value of the oxygen concentration is applied in execution of a fine control process, such as air-fuel ratio feedback control employing an observer, it is preferred that the oxygen concentration is sampled at a timing at which a change in the output from the LAF sensor 17 can be grasped as accurately as possible, with a time lag before exhaust gases emitted from the combustion chamber reach the LAF sensor 17, the response time of the LAF sensor 17, operating conditions of the engine, such as the engine rotational speed NE, and so forth taken into account. To this end, in view of the fact that the air-fuel ratio can be best sampled at timing corresponding to a maximal value thereof, the timing map is set such that as the engine rotational speed NE is lower and/or the intake pipe absolute pressure PBA is higher, a value sampled at an earlier crank angle position is selected. The word "earlier" means "closer to the immediately preceding TDC position of the cylinder" (i.e. an "older" sampled value is selected).

Then, the program proceeds to a step S602, wherein it is determined whether or not the flag FAFINH assumed 1 when the detected value of the oxygen concentration was stored in the storage area ZN of the ring buffer memory which has been selected at the step S601. If the flag FAFINH did not assume 1, the value stored at the storage area ZN is adopted without making a correction of the same (e.g. if ZN=Z8 in FIG. 5, the value stored at the storage area Z8 is adopted) at a step S603, followed by terminating the program. On the other hand, if the flag FAFINH assumed 1, a value EST obtained by interpolation (interpolated value) is adopted at a step S604, followed by terminating the program.

The interpolated value EST can be calculated by the use of the following equation (2) (by so-called linear interpolation) based e.g. on the number of a storage area ZA (Z5 in the FIG. 5 example) in which a value (sample) of the oxygen concentration detected immediately before the start of the internal resistance-detecting period is stored, a value "a" stored in the storage areas ZA, the number of a storage area ZB (Z0 in the FIG. 5 example) in which a value of the oxygen concentration detected immediately after the end of the internal resistance-selecting period is stored, and a value "b" stored in the storage area ZB:

$$EST=((ZA-ZN)b-(ZB-ZN)a)/(ZA-ZB) \quad (2)$$

By the above manner of selection of the detected value of oxygen concentration, it is possible to estimate the concentration of oxygen present in exhaust gases during the internal resistance-detecting period. It should be noted that a method other than the above interpolation method may be employed to estimate the oxygen concentration.

According to the present embodiment, as described above, in the oxygen concentration-detecting process based on the output from the LAF sensor, the detected value of the oxygen concentration can be directly obtained during the oxygen concentration-detecting period, whereas during the internal resistance-detecting period during which the actual oxygen concentration cannot be detected, the oxygen concentration can be estimated. As a result, as compared with the manner of adopting a detected value of the oxygen concentration (held value) detected immediately before the start of the internal resistance-detecting period, the difference between the held value of the oxygen concentration and the actual value of the same can be reduced, whereby a more accurate detected value of the oxygen concentration can be supplied to a control system which demands detected values of the oxygen concentration sampled at a very short sampling period. This makes it possible to reach the full potentials of various types of fine control which use detected values of the oxygen concentration from the LAF sensor.

Although in the above embodiment, the sampling period at which the detected value of the oxygen concentration is sampled is made synchronous with generation of each CRK signal, this is not limitative, but the sampling period may be set to any suitable period insofar as it is shorter than the switching period T.

Next, a second embodiment of the invention will be described with reference to FIGS. 7 to 9.

The second embodiment is distinguished from the first embodiment in that the switching period T for changing over between the LAF sensor-activating process and the oxygen concentration-detecting process (internal resistance detection repetition period) is set depending upon operating conditions of the engine by a process described in detail hereinafter. The hardware construction of the second embodiment is identical with that of the first embodiment shown in FIGS. 1 and 2. Therefore, component parts and elements corresponding to those of the first embodiment are designated by identical reference numerals, and detailed description thereof is omitted.

Figure 7:
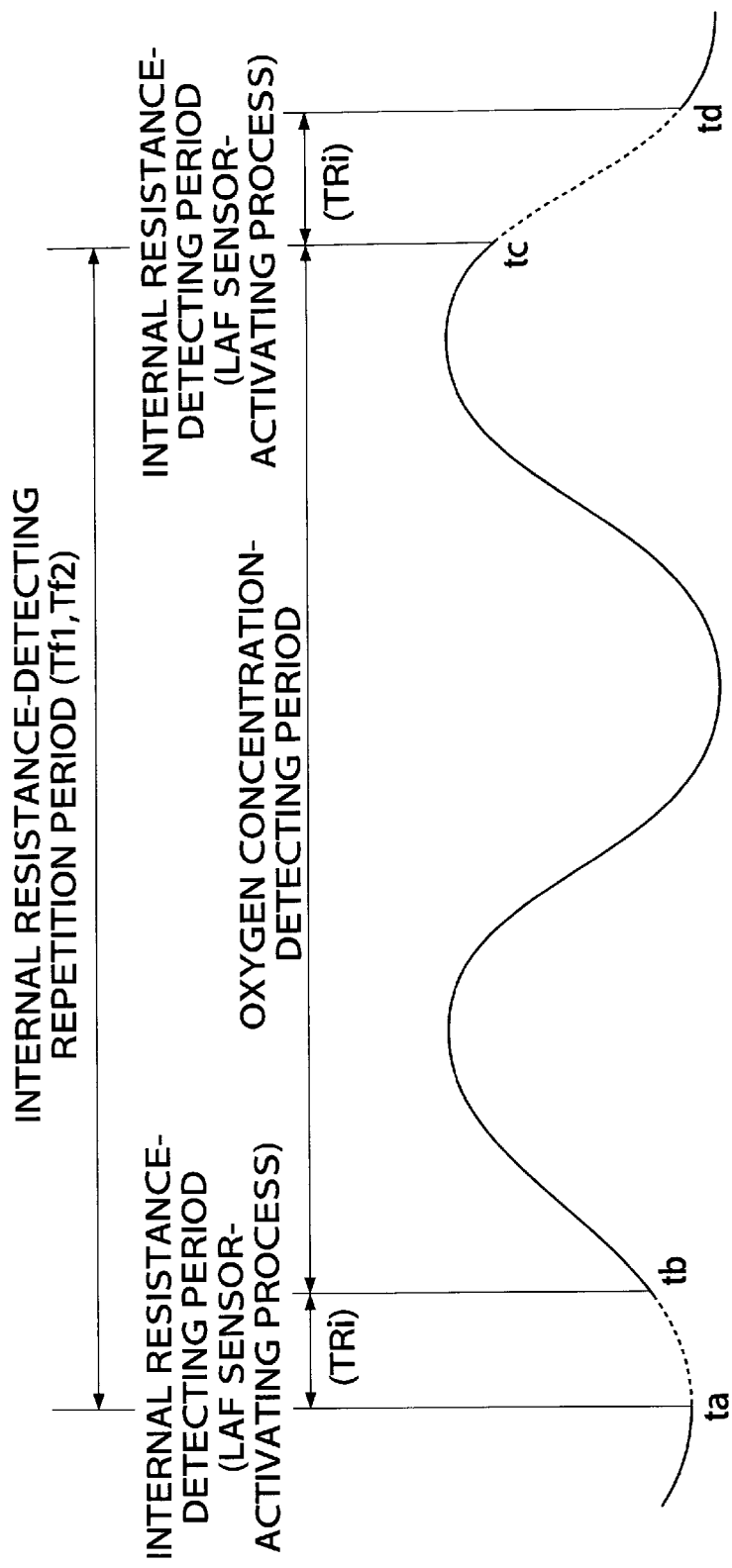
FIG. 7 is a diagram which is useful in explaining timing for switching between the LAF sensor-activating process and an oxygen concentration-detecting process according to a second embodiment of the invention.

FIG. 7 shows switching timing for switching between the LAF sensor-activating process and the oxygen concentration-detecting process. In the figure, the time period between time points tb and tc corresponds to the oxygen concentration-detecting period, while the solid line portions of the curve represent changes in the detected oxygen concentration value. The time period between time points ta and tb, and the time period between time points tc and td correspond to respective internal resistance-detecting periods (equivalent to a predetermined value Tri, referred to hereinbelow) during which the detection of the oxygen concentration is suspended. The oxygen concentration-detecting period and the internal resistance-detecting period alternately take place, with the switching period T (time period between time points ta and tc shown in FIG. 7) set depending upon operating conditions of the engine.

Figure 8:
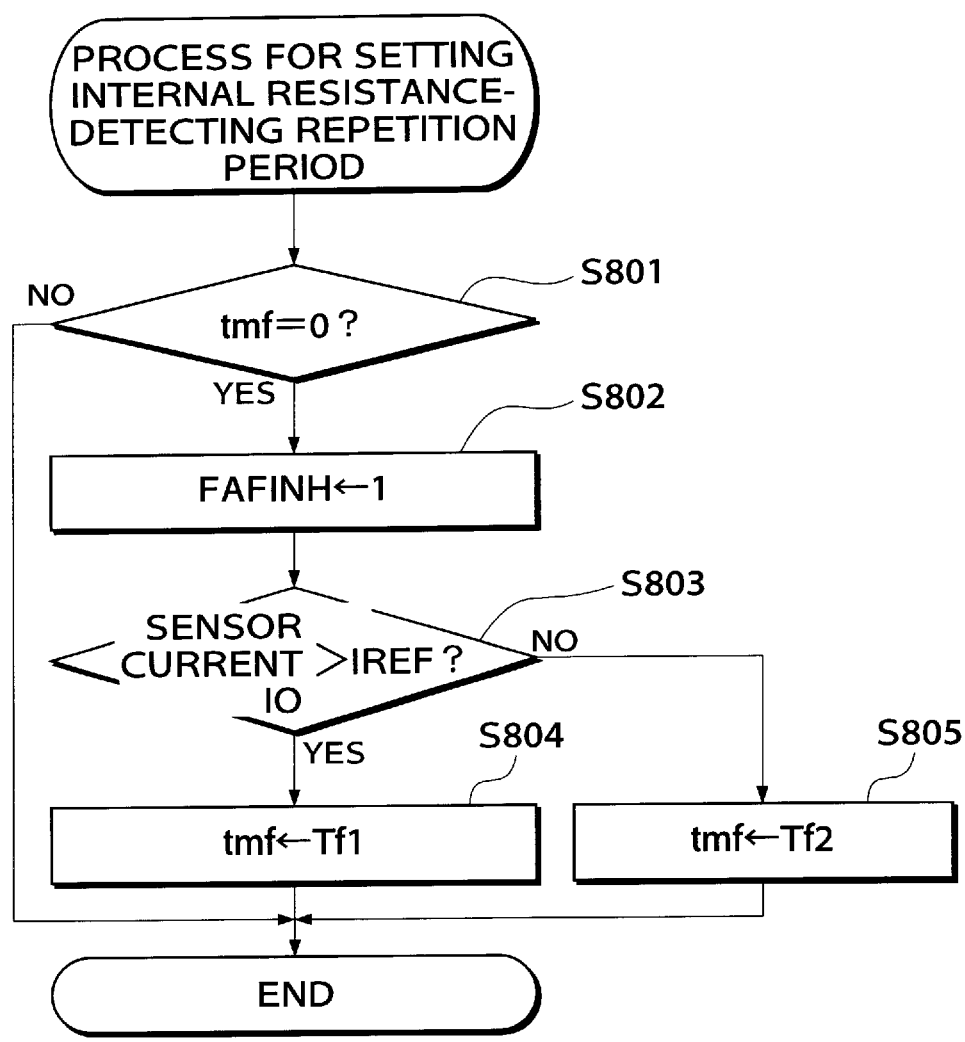
FIG. 8 is a flowchart showing a routine for carrying out a process for setting an internal resistance detection repetition period, according to the second embodiment.

FIG. 8 shows a routine for carrying out a process for setting the internal resistance detection repetition period, which is executed by the control block 69 of the second embodiment at predetermined time intervals set by a timer.

First, it is determined at a step S801 whether or not an internal resistance detection repetition period timer tmf has counted down to 0. If the count of the internal resistance detection repetition period timer tmf is not equal to 0, the program is immediately terminated, whereas if the same is equal to 0, a flag FAFINH, which, when set to 1, indicates that it is within the time period for executing the LAF sensor-activating process, is set to 1 at a step S802, and then it is determined at a step S803 whether or not an output current value I0 from the LAF sensor 17 obtained when a predetermined positive voltage for detecting the concentration of oxygen present in exhaust gases is applied to the LAF sensor is larger than a predetermined reference value IREF. Here, the predetermined reference value IREF is set to a threshold value (e.g. 10 mA) for determining whether or not the engine is operating in a predetermined lean operating region, e.g. whether or not the engine is in a fuel-cut condition. If I0>IREFF holds, it is determined that the engine is in the predetermined lean operating region. Alternatively, the air-fuel ratio of the mixture supplied to the engine may be calculated based on the output current value I0, to thereby determine that the engine is in the predetermined lean operating region if the calculated air-fuel ratio is larger than a predetermined value (e.g. A/F=20).

If I0>IREF holds at the step S803, the resistance detection repetition period Timer tmf is set to a first repetition period Tf1 (e.g. 128 ms) and started at a step S804, followed by terminating the program, whereas if I0≦IREFF holds, the same is set to a second repetition period Tf2 (e.g. 256 ms) longer than the first repetition period Tf1 and started at a step S805, followed by terminating the program. Thus, when the engine is operating in the predetermined lean operating region, e.g. when the temperature of exhaust gases suddenly changes due to fuel cut or the like, the temperature control of the LAF sensor is carried out with a higher priority. That is, the internal resistance detection repetition period is shortened, whereby the temperature control of the limit current oxygen sensor (LAF sensor in the present embodiment) is positively executed without delay. On the other hand, when the engine is not operating in the predetermined lean operating region, e.g. when the normal air-fuel ratio feedback control is being carried out, the internal resistance detection repetition period is increased, thereby securing a prolonged time period for detecting the oxygen concentration (oxygen concentration-detecting period). Further, it is preferred that the first repetition period Tf1 and the second repetition period Tf2 are set to optimal periods according to the heat capacities of the sensor element of the LAF sensor and the heater 54, the cooling characteristic of the LAF sensor 17, and the activation temperature range of the LAF sensor 17.

Figure 9:
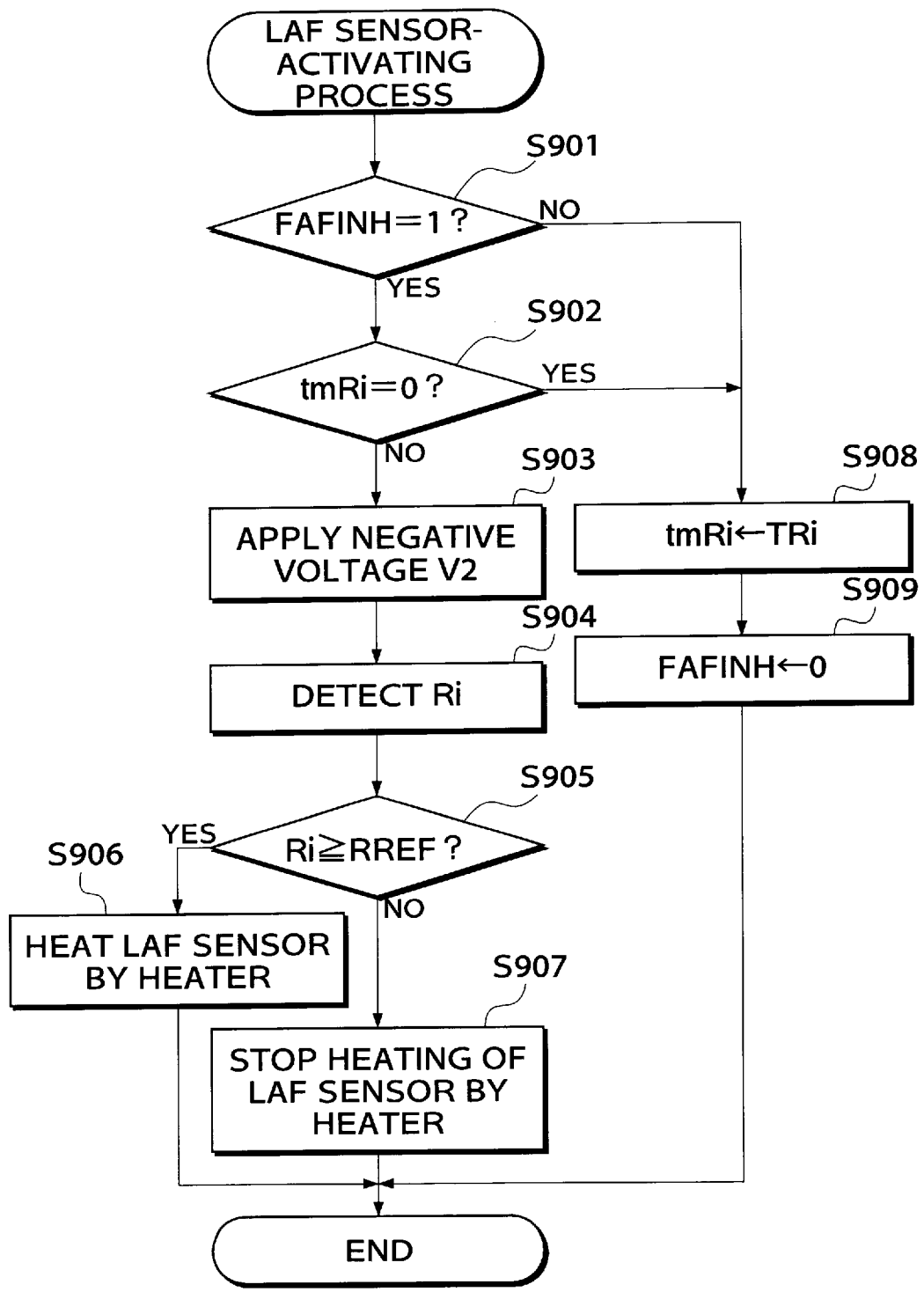
FIG. 9 is a flowchart showing a routine for carrying out a LAF sensor-activating process, according to the second embodiment.

FIG. 9 shows a routine for carrying out a LAF sensor-activating process, which is executed by the control block 69 of the second embodiment, at predetermined time intervals set by a timer.

First, it is determined at a step S901 whether or not the flag FAFINH assumes 1. If the flag FAFINH assumes 1, it is determined at a step S902 whether or not an internal resistance-detecting period timer tmRi set at a step 908, referred to hereinafter, has counted down to 0. If the flag FAFINH does not assume 1, or if the count of the internal resistance-detecting period timer tmRi is equal to 0, the internal resistance-detecting period timer tmRi is set to a predetermined value TRi (e.g. 4.5 ms) and started at a step S508, and then the flag FAFINH is set to 0, followed by terminating the program.

On the other hand, if the count of the-internal resistance-detecting period timer tmRi is not equal to 0 at the step S902, the internal resistance Ri of the LAF sensor 17 is detected at steps S903 and S904 in the following manner:

That is, the selector switch 66 is connected to the negative bias resource 65, whereby the predetermined negative voltage V2 is applied to the LAF sensor 17 at the step S903. Then, the value I2 of output current from the LAF sensor 17 is detected by the current-detecting block 67, and the signal indicative of the detected current value I2 is amplified and shaped by the amplifier 72, followed by being converted into a digital signal by the A/D converter 68. The internal resistance Ri of the LAF sensor is detected based on the digital value of the detected current value I2 at a step S904.

Then, it is determined at a step S905 whether or nor the detected internal resistance Ri of the LAF sensor 17 is equal to or larger the predetermined reference value RREF. If Ri≧RREF holds, the heating control block 71 is instructed to cause the heater 54 to heat the LAF sensor 17 at a step S506, followed by terminating the program, whereas if Ri<RREF holds, the heating control block 71 is instructed to cause the heater 54 to stop heating the LAF sensor 17 at a step S507, followed by terminating the program. Thus, the temperature of the LAF sensor 17 is controlled such that it is constantly within the activation temperature range.

According to the above process, the LAF sensor-activating process is carried out at the predetermined repetition period (whenever the flag FAFINH assumes 1) only over the predetermined time period (Tri).

In the present embodiment as well, similarly to the first embodiment, the process for storing-detected values of the oxygen concentration is carried out by the control block 69 in synchronism with generation of each CRK signal pulse according to the FIG. 4 routine described above.

According to the second embodiment, when the engine is in an operating condition leading to a sudden change in the temperature of exhaust gases emitted therefrom, e.g. when fuel cut is being executed, the internal resistance detection repetition period is shortened, whereby the control of the temperature of the LAF sensor can be positively carried out without delay, and at the same time degradation of the accuracy of detecting the oxygen concentration can be avoided. Moreover, during the normal air-fuel ratio feedback control, the internal resistance detection repetition period is increased to thereby secure a prolonged time period for detecting the oxygen concentration. As a result, it is possible to minimize adverse effects of provision of the oxygen concentration detection suspension period, while maintaining the accuracy of detection of the oxygen concentration. This makes it possible to enhance the controllability of the air-fuel ratio feedback control or the like by a control system for internal combustion engines, which utilizes the output from the LAF sensor.

Next, a third embodiment of the invention will be described with reference to FIG. 10. The oxygen concentration-detecting device according to the third embodiment is constructed similarly to the first and second embodiments described hereinabove with reference to FIGS. 1 and 2. This embodiment is distinguished from the second embodiment only in the process for setting the internal resistance detection repetition period, and therefore only this process will be described with reference to FIG. 10.

Figure 10:
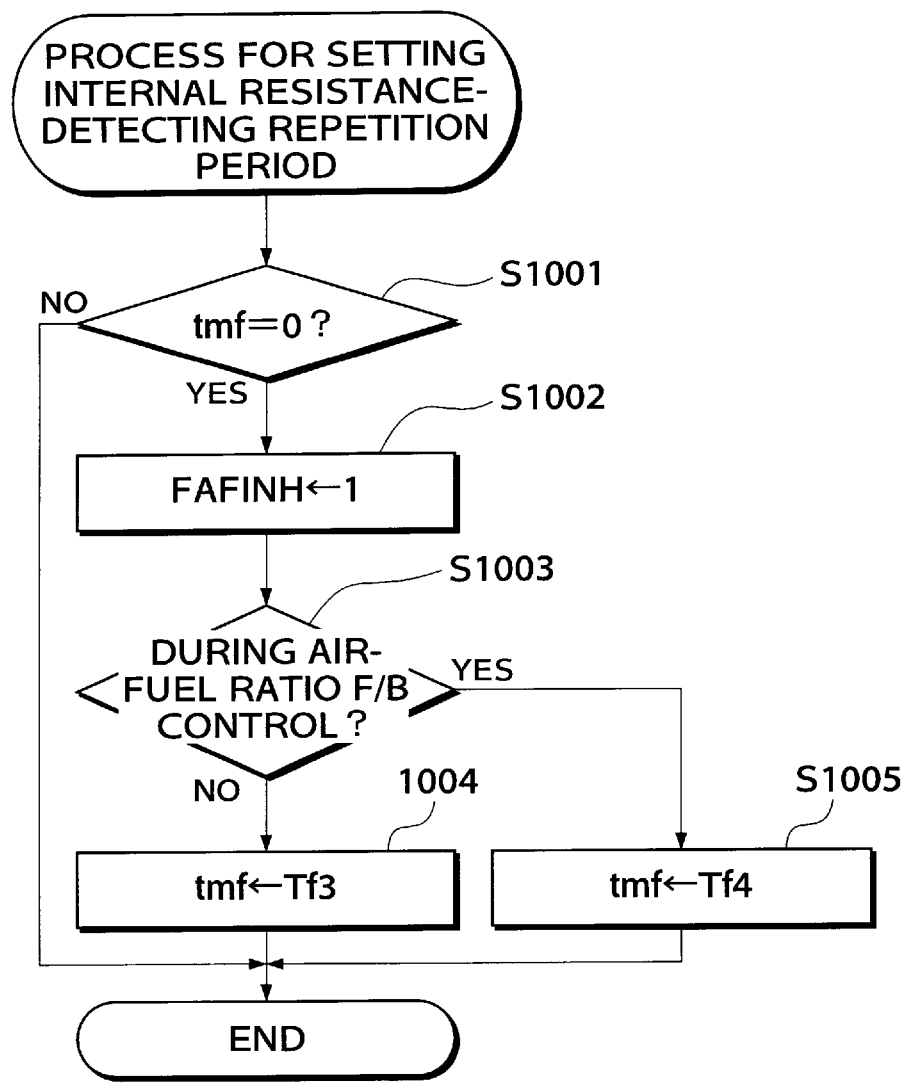
FIG. 10 is a flowchart showing a routine for carrying out a process for setting the internal resistance detection repetition period, according to a third embodiment of the invention.

FIG. 10 shows a routine for carrying out the process for setting the internal resistance detection repetition period, which is executed by the control block 69 of the third embodiment, at predetermined time intervals set by a timer.

First, at steps S1001 and S1002, the same processes as executed at the steps S801 and S802 in FIG. 8 are carried out.

Then, the program proceeds to a step S1003, wherein it is determined whether or not the air-fuel ratio feedback control is being carried out. If the air-fuel ratio feedback control is not being carried out, the internal resistance detection repetition period timer tmf is set to a third repetition period Tf3 (e.g. 128 ms) and started at a step S1004, followed by terminating the program, whereas if the air-fuel ratio feedback control is being carried out, the internal resistance detection repetition period timer tmf is set to a fourth repetition period Tf4 (e.g. 256 ms) longer than the third repetition period Tf3 and started at a step S1005, followed by terminating the program.

According to the third embodiment, when the air-fuel ratio open-loop control is being carried out, the internal resistance detection repetition period is shortened, whereby the temperature control of the LAF sensor can be positively carried out without delay, while avoiding the accuracy of detection of the oxygen concentration from being degraded. Further, during the execution of the air-fuel ratio feedback control, the internal resistance detection repetition period is increased to thereby secure a prolonged time period for detecting the oxygen concentration. As a result, it is possible to obtain substantially the same effects as obtained by the second embodiment.

Further, although in the second and third embodiments, two predetermined values (Tf1 and Tf2; Tf3 and Tf4) are provided for the internal resistance detection repetition period, this is not limitative, but more than two values of the internal resistance detection repetition period may be provided for selection in dependence on operating conditions of the engine. The operating parameter or parameters of the engine for selecting the value of the internal resistance detection repetition period are not limited to those employed in the above embodiments.

The oxygen concentration-detecting device according to the present invention is particularly useful when it is applied to an air-fuel ratio feedback control system or the like for internal combustion engines, which performs fine control based on a modern control theory by using a controller of a recurrence formula type, such as an observer and an optimal regulator. In such an application, the detected value of the oxygen concentration, which is selected by the FIG. 6 routine, is converted to an equivalent ratio which is equivalent to the actual air-fuel ratio (actual equivalent ratio), and the actual equivalent ratio is used in the feedback control. This enables the observer to estimate the air-fuel ratios of exhaust gases from the cylinders cylinder by cylinder with higher accuracy, thereby preventing divergence of the cylinder-by-cylinder air-fuel ratio feedback control, but enhancing the convergence of the cylinder-by-cylinder air-fuel ratio to a desired air-fuel ratio. Further, the use of the actual equivalent ratio obtained from the selected detected oxygen concentration value described above enables the adaptive control by the optimal regulator or the like to compensate for the response delay of the LAF sensor with higher accuracy.

Further, it is desirable to apply the oxygen concentration-detecting device according to the present invention to any other control systems insofar as the control systems use the output from the limit current oxygen sensor. In such an application, the timing map for selecting the detected value of the oxygen concentration is suitably set according to the contents of control by the control systems.

What is claimed is:

1. In an oxygen concentration-detecting device for detecting concentration of oxygen present in exhaust gases emitted from an internal combustion engine, including an oxygen sensor of a limit current type, heating means for heating said oxygen sensor, oxygen concentration-detecting means for applying a first voltage to said oxygen sensor and detecting said concentration of oxygen based on a first output current from said oxygen sensor obtained when said first voltage is applied to said oxygen sensor, internal resistance-detecting means for applying a second voltage to said oxygen sensor for a predetermined period at a first repetition period and detecting internal resistance of said oxygen sensor based on a second output current from said oxygen sensor obtained when said second voltage is applied to said oxygen sensor, and heating control means for controlling heating of said oxygen sensor by said heating means based on said internal resistance of said oxygen sensor detected by said internal resistance-detecting means, the improvement comprising:
    memory means for sampling values of said concentration of oxygen based on said first output current from said oxygen sensor at a second repetition period shorter than said first repetition period and storing sampled values of said concentration of oxygen; and
    oxygen concentration-estimating means for estimating said concentration of oxygen based on said sampled values of said concentration of oxygen stored in said memory means when said second voltage is applied to said oxygen sensor.

2. An oxygen concentration-detecting device according to claim 1, wherein said oxygen concentration-estimating means estimates said concentration of oxygen by an interpolation based on one of said sampled values of said concentration of oxygen sampled immediately before said second voltage was applied to said oxygen sensor by said internal resistance-detecting means and stored in said memory means, and another one of said sampled values of said concentration of oxygen sampled immediately after said second voltage ceased to be applied to said oxygen sensor by said internal resistance-detecting means and stored in said memory means.

3. An oxygen concentration-detecting device according to claim 2, wherein said memory means has a predetermined number of storage areas, and stores said one of said sampled values of said concentration of oxygen sampled immediately before said second voltage was applied to said oxygen sensor by said internal resistance-detecting means sequen-tially into corresponding ones of said storage areas over a time period during which said internal resistance-detecting means detects said internal resistance of said oxygen sensor.

4. An oxygen concentration-detecting device according to claim 3, including selecting means for selecting one of said storage areas from which one of said sampled values of said concentration of oxygen is to be read out in dependence on operating conditions of said engine.

5. An oxygen concentration-detecting device according to claim 3, wherein said interpolation is carried out by using a number assigned to one of said storage areas which stores said one of said sampled values of said concentration of oxygen sampled immediately before said second voltage was applied to said oxygen sensor by said internal resistance-detecting means, said one of said sampled values of said oxygen concentration stored in said one of said storage areas, a number assigned to another one of said storage areas which stores said another one of said sampled values of said concentration of oxygen sampled immediately after said second voltage ceased to be applied to said oxygen sensor by said internal resistance-detecting means, and said another one of said sampled values of said oxygen concentration stored in said another of said storage areas.

6. In an oxygen concentration-detecting device for detecting concentration of oxygen present in exhaust gases emitted from an internal combustion engine, including an oxygen sensor of a limit current type, heating means for heating said oxygen sensor, detecting means for applying a first voltage to said oxygen sensor, detecting said concentration of oxygen present in exhaust gases emitted from said engine based on a first output current from said oxygen sensor obtained when said first voltage is applied to said oxygen sensor, applying a second voltage to said oxygen sensor for a predetermined period at a predetermined repetition period, and detecting internal resistance of said oxygen sensor based on a second output current from said oxygen sensor obtained when said second voltage is applied thereto, and heating control means for controlling heating of said oxygen sensor by said heating means based on said internal resistance of said oxygen sensor detected by said detecting means, the improvement comprising repetition period-setting means for setting said predetermined repetition period in dependence on operating conditions of said engine.

7. An oxygen concentration-detecting device according to claim 6, wherein when an air-fuel ratio of a mixture supplied to said engine assumes a lean value, said repetition period-setting means sets said predetermined repetition period to a shorter period than when said air-fuel ratio is richer than said lean value.

8. An oxygen concentration-detecting device according to claim 7, wherein said repetition period-setting means determines that said air-fuel ratio of said mixture assumes said lean value when said first output current from said oxygen sensor obtained when said first voltage is applied to said oxygen sensor is larger than a predetermined value.

9. An oxygen concentration-detecting device according to claim 6, wherein said repetition period-setting means sets said predetermined repetition period to a shorter period when air-fuel ratio feedback control responsive to said first output current from said oxygen sensor is not carried out than when said air-fuel ratio feedback control is carried out.

* * * * *